(12) United States Patent
Baxter et al.

(10) Patent No.: US 7,728,035 B2
(45) Date of Patent: Jun. 1, 2010

(54) ESTER DERIVATIVES OF RHEIN AND THEIR THERAPEUTIC USE

(75) Inventors: Andrew Douglas Baxter, Essex (GB); Andrea Walmsley, Essex (GB)

(73) Assignee: Sosei R&D Ltd., Essex (GB)

( * ) Notice: Subject to any disclaimer, the term of this patent is extended or adjusted under 35 U.S.C. 154(b) by 569 days.

(21) Appl. No.: 10/591,157

(22) PCT Filed: Mar. 4, 2005

(86) PCT No.: PCT/GB2005/000832

§ 371 (c)(1),
(2), (4) Date: Oct. 6, 2006

(87) PCT Pub. No.: WO2005/085170

PCT Pub. Date: Sep. 15, 2005

(65) Prior Publication Data

US 2007/0185036 A1 Aug. 9, 2007

(30) Foreign Application Priority Data

Mar. 4, 2004 (GB) ................. 0404953.2

(51) Int. Cl.
*A61K 31/21* (2006.01)
*C07C 49/593* (2006.01)

(52) U.S. Cl. ................. 514/510; 552/293; 552/295

(58) Field of Classification Search ............ None
See application file for complete search history.

(56) References Cited

U.S. PATENT DOCUMENTS

| 4,244,968 A | 1/1981 | Friedmann |
| 6,124,358 A | 9/2000 | Estanove et al. |

FOREIGN PATENT DOCUMENTS

EP 0 822 177 A1 2/1998

OTHER PUBLICATIONS

Database Crossfire Bielstein, Bielstein Institut Zur Förderung Der Chemischen Wissenschaften, XP002331000, Database Accession No. 3499454, (1990).
Database Crossfire Bielstein, Bielstein Institut Zur Förderung Der Chemischen Wissenschaften, XP002331001, Database Accession No. 3514786, (1990).
Database WPI, AN 1984-034225, XP-002331004, Derwent Publications Ltd, (1984).

*Primary Examiner*—Patricia A Duffy
*Assistant Examiner*—Christopher R Stone
(74) *Attorney, Agent, or Firm*—Saliwanchik, Lloyd & Saliwanchik

(57) ABSTRACT

Compounds that may have anti-inflammatory activity are of general formula (I); wherein $X_1$, is H or $COR_1$, and $X_2$ is H or $COR_2$ but $X_1$, and $X_2$ are not both H; $R_1$ and $R_2$ are the same or different and are each $C_{1-4}$ alkyl substituted with $R_3$, or a four to seven-membered ring which can be optionally substituted with $R_8$ and can contain one or more additional heteroatoms selected from O, $S(O)_n$ and $NR_9$; is $R_3$ is F, $CF_3$, $OR_4$, $NR_5R_6$ O, $S(O)_n$ $R_7$; $R_4$, $R_5$ and $R_6$ are the same or different and are each H or $C_{1-4}$ alkyl optionally substituted with $R_3$, or $NR_5R_6$ is a $C_{4-6}$ heterocycloalkyl ring containing one or more heteroatoms selected from O, $NR_8$ and $S(O)_n$; each n is 0-2; $R_7$ is $C_{1-4}$ alkyl; $R_8$ is as defined for $R_3$ or $C_{1-4}$ alkyl optionally substituted with $R_3$ or halogen; and $R_9$ is H or $C_{1-4}$ alkyl; or a salt, solvate or hydrate thereof.

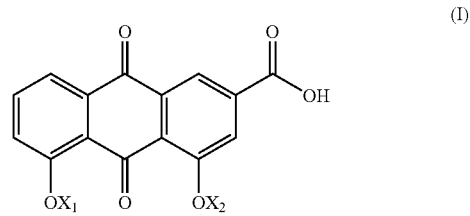

(I)

7 Claims, No Drawings

ESTER DERIVATIVES OF RHEIN AND THEIR THERAPEUTIC USE

CROSS-REFERENCE TO A RELATED APPLICATION

This application is a National Stage Application of International Application No. PCT/GB2005/000832, filed Mar. 4, 2005; which claims priority to Great Britain Applications No. 0404953.2, filed Mar. 4, 2004.

FIELD OF THE INVENTION

The present invention relates to novel dihydroxyanthraquinones which are ester derivatives of rhein, and to their therapeutic use.

BACKGROUND OF THE INVENTION

T-lymphocytes are known to play a central role in the pathogenesis of many inflammatory and autoimmune diseases, including rheumatoid arthritis. The activation of T-cells by antigen-presenting cells is the primary event in the initiation of the inflammatory process, which subsequently leads to the activation of other inflammatory cells and in turn the release of pro-inflammatory cytokines, chemotactic agents and matrix-degrading enzymes.

Multiple sclerosis is a chronic demyelinating inflammatory disease of the central nervous system. T-cell proliferation leads to release of the pro-inflammatory cytokines (primarily IL-2 and IFN-γ) and the recruitment of leucocytes (including macrophages) which orchestrate the inflammatory response.

In chronic obstructive pulmonary disease (COPD), activation of neutrophils and macrophages by proliferating CD8+ T-cells leads to the release of pro-inflammatory cytokines and elastin-degrading enzymes, which causes a chronic and progressive degradation of lung tissues and ultimately reduction in respiratory function.

Crohn's disease and ulcerative colitis are chronic inflammatory diseases of the intestines collectively known as inflammatory bowel disease (IBD). It is likely that both these disorders are actually heterogeneous groups of diseases that have different causes, but share similar perpetuating stimuli and common pathways of tissue injury. Once again, T-cells are central to the progression of this collection of diseases, leading to the activation of immune, mesenchymal and epithelial cells, recruitment of circulating effector cells and ultimately gastrointestinal tissue damage.

In psoriasis, the presentation of antigen by Langerhan's cells to CD4+ T-cells leads to the synthesis of cytokines which stimulate keratinocyte proliferation and the expression of adhesion molecules by endothelial cells and keratinocytes. Keratinocytes in turn are stimulated to produce their own cytokines which can act in an autocrine and/or paracrine manner to maintain the psoriatic process.

There is a similarly strong rationale for the central involvement of T-cells in many other inflammatory diseases, including systemic lupus erythematosus (SLE), asthma, lupus nephritis, glomerulonephritis, IgA nephropathy, gingivitis, periodontal disease, atopic dermatitis, scleroderma and graft vs host disease (GVHD). Thus, inhibitors of T-cell proliferation may have utility in the treatment of a range of inflammatory and autoimmune diseases.

Rhein (1,8-dihydroxyanthraquinone-3-carboxylic acid) is a well-characterised anti-inflammatory agent, with recognised utility in a range of inflammatory diseases. While this agent has not been demonstrated to inhibit T-cell proliferation, it is known to inhibit the production of pro-inflammatory cytokines (IL-1β and TNFα) in human osteoarthritic synovium and chondrocytes (J. Martel-Pelletier et al, *Journal of Rheumatology*, 1998, 25 (4), 753-762) and to inhibit cytokine gene expression in a model of lupus nephritis (S. Lemay et al, *Kidney International*, 1996, 50 (1), 85-93). In common with the tetracyclines, rhein and its pro-drug diacerein have been shown to down-regulate the production of pro-matrix metalloproteinases (pro-MMPs −1, −3, −9 and −13) while upregulating the production of tissue inhibitor of metalloproteinases −1 (TIMP-1) from rabbit articular chondrocytes (T. Tamura et al, *Osteoarthritis and Cartilage*, 2001, 9 (3), 257-263).

Rhein is disclosed as having utility in arthritis and multiple sclerosis (U.S. Pat. No. 4,346,103) and in diabetic nephropathy (EP0990441A1), diseases where over-production of IL-1β is particularly implicated. The widespread use of rhein has been somewhat limited by its rather poor physicochemical properties. This issue is not addressed completely with the well characterised pro-drug diacerein, where utility in the clinical setting is again limited by poor physicochemical properties (P. Nicolas et al, *Clin. Pharmacokinet.*, 1998, 35 (5), 347-359).

SUMMARY OF THE INVENTION

The present invention is related to the observation that simple ester derivatives of rhein are capable of inhibiting cytokine production and T-cell proliferation in assays where rhein itself and other simple derivatives fail to produce a response. It is likely that these agents will be of clinical utility in the wide range of inflammatory and autoimmune diseases described above, due to their improved physical properties over the parent compound.

The invention encompasses novel dihydroxyanthraquinones which may inhibit cytokine production and T-cell proliferation, and are therefore of utility in the treatment of T-cell mediated diseases including those described above.

In a first aspect of the invention, novel compounds are of general formula (I):

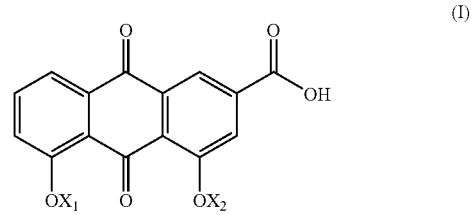

wherein $X_1$ is H or $COR_1$ and $X_2$ is H or $COR_2$ but $X_1$ and $X_2$ are not both H;

$R_1$ and $R_2$ are the same or different and are each $C_{1-4}$ alkyl substituted with $R_3$, or a four to seven-membered ring which can be optionally substituted with $R_8$ and can contain one or more additional heteroatoms selected from O, $S(O)_n$ and $NR_9$;

$R_3$ is F, $CF_3$, $OR_4$, $NR_5R_6$ or $S(O)_nR_7$;

$R_4$, $R_5$ and $R_6$ are the same or different and are each H or $C_{1-4}$ alkyl optionally substituted with $R_3$, or $NR_5R_6$ is a $C_{4-6}$ heterocycloalkyl ring containing one or more heteroatoms selected from O, $NR_8$ and $S(O)_n$;

each n is 0-2;

$R_7$ is $C_{1-4}$ alkyl;

$R_8$ is as defined for $R_3$ or $C_{1-4}$ alkyl optionally substituted with $R_3$ or halogen; and $R_9$ is H or $C_{1-4}$ alkyl;

and the salts, solvates and hydrates thereof.

Compounds of the invention may be diesters ($X_1$ is $COR_1$ and $X_2$ is $COR_2$; hereinafter formula 1) or monoesters where $X_1$ is H (formula 2) or $X_2$ is H (formula 3).

Further aspects of the invention include pharmaceutical compositions comprising the compounds of formula I, their use in therapy and, more particularly, their use in the treatment of inflammatory conditions.

DESCRIPTION OF THE INVENTION

It will be appreciated that the compounds according to the invention can contain one or more asymmetrically substituted carbon atoms. The presence of one or more of these asymmetric centres in a compound of formula (1), (2) and (3) can give rise to stereoisomers, and in each case the invention is to be understood to extend to all such stereoisomers, including enantiomers and diastereomers, and mixtures including racemic mixtures thereof.

The term "$C_{1-4}$ alkyl" refers to a straight or branched chain alkyl moiety having from one to four carbon atoms, including for example, methyl, ethyl, propyl, isopropyl, butyl, tert-butyl and the like.

The term "$C_{4-6}$ heterocycloalkyl" refers to a saturated heterocyclic moiety having from three to six carbon atoms and one or more heteroatom from the group N, O, S and includes for example azetidinyl, oxetidinyl, pyrrolidinyl, tetrahydrofuranyl, piperidinyl, tetrahydropyranyl and the like.

The term "halogen" means fluorine, chlorine, bromine or iodine.

Salts of compounds of formula (1), (2) and (3) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

A carboxyl group can be protected in the form of a readily cleavable ester such as the methyl, ethyl, benzyl or tert-butyl ester.

Compounds of the formulae (1), (2) and (3) may be prepared by any suitable method known in the art and/or by the following processes. It will be appreciated that where a particular stereoisomer of formula (1), (2) or (3) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below, the groups $R_1$, $R_2$, $R_3$, $R_4$, $R_5$, $R_6$ $R_7$, $R_8$ and $R_9$ are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wuts.

A process for preparing compounds of formula (1) comprises conversion of the activated ester in the presence of base (such as diacerein to rhein), followed by reaction with the required activated acid such as acid chloride or anhydride. The carboxylic acid can be reduced to give the alcohol and the hydroxyl group further substituted, or desired amides can be formed by reacting the carboxylic acid or activated acid with suitable amines. Diacerein and the corresponding activated acids are either commercially available or readily obtained from commercially available materials by those skilled in the art of synthetic organic chemistry.

A process for preparing compounds of general formulae (2) and (3) will be similar to that described for (1), but will necessitate the additional steps of selectively protecting one hydroxyl group prior to the reaction with the acid chloride, and this will have to be followed by a deprotection step to reveal the target compound.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

Compounds of the invention exhibit in vitro inhibiting activities with respect to T-cell proliferation. Compounds according to the invention also exhibit in vitro inhibition of pro-inflammatory cytokine release. The activity of the compounds may be determined by use of the appropriate cellular assay, for example as described below.

This invention also relates to a method of treatment for patients (including man and/or mammalian animals raised in the dairy, meat or fur industries or as pets) suffering from disorders or diseases which can be attributed to T-cell proliferation as previously described, and more specifically, a method of treatment involving the administration of the T-cell proliferation inhibitors of formula (1), (2) or (3) as the active constituents.

As mentioned above, compounds of formula (1), (2) and (3) are useful in human or veterinary medicine, since they are active as inhibitors of T-cell proliferation. Accordingly in another aspect, this invention concerns:

a method of management (by which is meant treatment or prophylaxis) of disease or conditions mediated by T-cells in mammals, in particular in humans, which method comprises administering to the mammal an effective amount of a compound of formula (1), (2) or (3) above, or a pharmaceutically acceptable salt thereof; and a compound of formula (1), (2) or (3) for use in human or veterinary medicine, particularly in the management (by which is meant treatment or prophylaxis) of diseases or conditions mediated by T-cells; and the use of a compound of formula (1), (2) or (3) in the preparation of an agent for the management (by which is meant treatment or prophylaxis) of diseases or conditions mediated by T-cells.

The disease or conditions referred to above include inflammatory and autoimmune diseases such as rheumatoid arthritis, osteoarthritis, osteoporosis, inflammatory bowel disease including ulcerative colitis and Crohn's disease, ulcerative colitis, multiple sclerosis, periodontitis, gingivitis, graft versus host reactions, psoriasis, scleroderma, atopic dermatitis, asthma, systemic lupus erythematosus (SLE), nephropathy and chronic obstructive pulmonary disease (COPD). Dermal conditions that may be treated include those given above, and also psoriatic arthritis, epidermolysis bullosa, atopic dermatitis and vasculitis. Anti-angiogenic activity may allow the treatment of conditions such as age-related macular degeneration and cancer.

For the treatment of rheumatoid arthritis, multiple sclerosis and other diseases and indications resulting from the overactivity of T-cells such as those highlighted above, the compounds of formula (1), (2) or (3) may be administered orally, topically, parenterally, by inhalation or nasal spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

A pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyeryl distearate may be employed. They may also be coated by the techniques described in U.S. Pat. No. 4,256,108, U.S. Pat. No. 4,166,452 and U.S. Pat. No. 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formulae (1), (2) and (3) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of formulae (1), (2) and (3) are employed. For purposes of this specification, topical application includes mouth washes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples illustrate the invention.

EXAMPLE 1

4,5-Bis(tetrahydropyran-4-carbonyloxy)-9,10-dioxo-dihydroanthracene-2-carboxylic acid 1. 4,5-Dihydroxy-9,10-dioxoanthracene-2-carboxylic acid Diacerein (150 g, 0.41 mol) was stirred in 10% (w/w) $Na_2CO_3$ solution (4 L) resulting in a red mixture. After stirring overnight the mixture was acidified to pH2 with 5M HCl solution to give a yellow precipitate. This was filtered and dried in a vac-oven at 50° C. (168 g,>100%).

$^1$H NMR (400 MHz, DMSO): 7.40 (1H, d J=8 Hz), 7.71-7.76 (2H, m), 7.82 (1H, t J=8 Hz), 8.11 (1H, d J=1.6 Hz).

2. Tetrahydropyran-4-ylcarboxylic acid

Methyl tetrahydro-2H-pyran-4-carboxylate (270 g, 1.87 mol) was diluted in ethanol (2 L). A 1M aqueous LiOH solution (1870 ml, 1.87 mol) was added (slight exotherm) at RT and the reaction was stirred for 3 hrs. The reaction mixture was concentrated to ca. 1 L and acidified to pH 2 with 5M HCl solution. The aqueous solution was extracted with ethyl acetate (3×600 ml) and the organic layer was dried ($MgSO_4$) and evaporated to dryness to give a white solid (230.3 g, 94%).

$^1$H NMR (400 MHz, $CDCl_3$): 1.71-1.89 (4H, m), 2.54-2.59 (1H, m), 3.38-3.48 (2H, m), 3.91-3.99 (2H, m).

3. Tetrahydro-4-pyranyl chloride

Tetrahydropyran-4-yl-carboxylic acid (230 g) was dissolved in thionyl chloride (1500 ml) and refluxed for 2.5 hrs. After this time the mixture was cooled to room temperature and evaporated to dryness. Toluene (500 ml) was added to the resulting oil and the mixture was evaporated to dryness to give a light green oil. This was used in the next stage without purification.

4. 4,5-Bis(tetrahydropyran-4-carbonyloxy)-9,10-dioxo-dihydroanthracene-2-carboxylic acid 4,5-Dihydroxy-9,10-dioxoanthracene-2-carboxylic acid (168 g) was stirred in pyridine (5 L) at RT resulting in a brown suspension. The acid chloride (209 g, 1.41 mol) was added over 10 min and the reaction was stirred at RT for 48 h. The reaction mixture was split into 5 equal batches and each was added slowly to 3M HCl solution (3.75 L) with ice-cooling giving a yellow precipitate. The mixtures were filtered and the combined solid was triturated with acetone (2×600 ml). The resulting solid was dried in a vac-oven at 50° C. (173 g, 83%).

$^1$H NMR (400 MHz, DMSO): 1.78-1.86 (4H, m), 1.97-2.01 (4H, m), 2.91-2.93 (2H, m), 3.43-3.46 (4H, m), 3.92-3.96 (4H, m), 7.59 (1H, d J=7.6 Hz), 7.85-7.91 (1H, t J=7.6 Hz), 8.00 (1H, s), 8.10 (1H, d J=7.6 Hz), 8.52 (1H, s). ESI: 509 (M +H$^+$).

The following Examples were conducted in a similar way.

EXAMPLE 2

4,5-Bisbutyryloxy-9,10-dioxo-9,10-dihydroanthracene-2-carboxylic acid 4,5-Dihydroxy-9,10-dioxoanthracene-2-carboxylic acid (3.0 g) was suspended in pyridine (100 ml) and stirred at RT for 30 mins. Butyryl chloride was added (3.6 g, 5 equiv.) to give a clear reaction mixture which was stirred at RT over the weekend. The reaction mixture was reduced to a smaller volume and quenched with 2M HCl (200 ml), adjusting the pH to pH 2. An orange solid was isolated by filtration. This solid was slurried in water (30 ml) followed by ethyl acetate (30 ml) and dichloromethane (30 ml), and isolated by filtration as a yellow solid (2.0 g, 45%).

$^1$H NMR (DMSO): 1.1 (6H, m), 1.8 (4H, m), 2.6 (4H, m), 7.7 (1H, d), 7.9-8.1 (2H, m), 8.3 (1H, m), 8.6 (1H, d). ESI [M+H]$^+$425

EXAMPLE 3

4,5-Bis(2-benzyloxyacetyloxy)-9,10-dioxo-9,10-dihydroanthracene-2-carboxylic acid 4,5-Dihydroxy-9,10-dioxoanthracene-2-carboxylic acid (3.0 g) was suspended in pyridine (100 ml) and stirred at RT for 30 mins. Benzyloxyacetyl chloride (3.6 g, 5 equiv.) was added, to give a clear reaction mixture which was stirred at RT over the weekend. The reaction mixture was reduced to a smaller volume and quenched with 2M HCl (200 ml), adjusting the pH to pH 2. An orange solid was isolated by filtration. This crude solid was slurried in water (30 ml), followed by ethyl acetate (30 ml) and dichloromethane (30 ml). A yellow solid was isolated by filtration (3.6 g, 61%).

$^1$H NMR (DMSO): 4.6 (4H, s), 4.7 (4H, s), 7.3-7.5 (10H, m), 7.7 (1H, d), 8.0 (1H, m), 8.2 (2H, m), 8.6 (1H, d)

EXAMPLE 4

4,5-Bis(4-methoxybutyryloxy)-9,10-dioxo-9,10-dihydroanthracene-2-carboxylic acid 1. 4-Methoxybutyronitrile Sodium methoxide (22 g) was charged to a reaction vessel, methanol was added and the reaction mixture stirred at RT for 30 mins. The mixture was cooled to <5° C. (ice bath), and a solution of 4-bromobutyronitrile (20 g) in methanol (100 ml) was added dropwise. Upon complete addition, the reaction mixture was allowed to warm to RT and stirred overnight. The reaction mixture was then hydrolysed immediately without isolation.

2. 4-Methoxybutyric acid

To a stirred solution of 4-methoxybutyronitrile was added dropwise a solution of potassium hydroxide (22 g) in water (220 ml). Upon complete addition, the reaction was heated to reflux temperature and held at this temperature overnight. The reaction mixture was then cooled to RT, and the pH adjusted to pH 2 by the addition of 2M HCl. The reaction mixture was then extracted into ethyl acetate (2×500 ml). The combined organics were dried over magnesium sulfate, filtered and concentrated in vacuo. Purification by silica gel column chromatography (1:1 ethyl acetate/hexane) gave the required material as a colourless oil (10.2 g, 62% over 2 steps).

3. 4-Methoxybutyryl chloride

4-Methoxybutyric acid (10 g) in toluene (50 ml) was added dropwise to a stirred solution of oxalyl chloride (8 ml) in toluene (50 ml) at ice bath temperature. Upon complete addition, the reaction was allowed to warm to RT and stirred overnight. Reaction mixture was evaporated to dryness to give the product which was used immediately.

4. 4,5-Bis(4-methoxybutyryloxy)-9,10-dioxo-9,10-dihydroanthracene-2-carboxylic acid To a stirred suspension of 4,5-dihydroxy-9,10-dioxoanthracene-2-carboxylic acid (1 g) in pyridine (30 ml) was added 4-methoxybutyryl chloride (2 g). The reaction was stirred at RT for 2 days, and as TLC indicated that starting acid was still present, a further 2 g of the acid chloride was added. Reaction was complete after a further 2 days at RT. The reaction mixture was evaporated to dryness and stirred in 2M HCl (30 ml) for 30 mins. The resultant crude solid was isolated by filtration. This was then slurried with water (30 ml) followed by ethyl acetate (30 ml). The solid was isolated by filtration and oven dried overnight to give 1.0 g (59%).

ESI [M+H]$^+$484. 1H (DMSO): 1.8-2.0 (4H, m), 2.7-2.9 (4H, m), 3.3 (6H, s), 3.4-3.5 (4H, m), 7.6 (1H, d), 7.9 (1H, m), 8.0 (1H, d), 8.1 (1H, d), 8.5 (1H, d)

EXAMPLE 5

4,5-Bis(tetrahydrofuran-3-carbonyloxy)-9,10-dioxo-9,10-dihydroanthracene-2-carboxylic acid Tetrahydrofuroic acid (10 g) in toluene (50 ml) was added to a solution of oxalyl chloride (8.1 ml) in toluene (50 ml) and DMF (1 drop), dropwise at ice bath temperature. Upon complete addition the reaction was allowed to warm to RT and stirred overnight. The reaction mixture was then concentrated in vacuo to give tetrahydro-3-furyl chloride as a yellow oil (9.4 g, 81 %).

To a stirred suspension of 4,5-dihydroxy-9,10-dioxoanthracene-2-carboxylic acid (2 g) in pyridine (100 ml) was added tetrahydro-3-furyl chloride (2.1 g) in dichloromethane (10 ml) dropwise at ice bath temperature. Upon complete addition, the reaction mixture was stirred at RT overnight under an inert atmosphere. A further 2.2 equiv of the acid chloride were then added to drive the reaction to completion. After a further 3 hours at RT, the reaction mixture was reduced to a smaller volume (approx 20 ml), and 2M HCl (100 ml) added. The reaction mixture was then filtered to give a yellow solid which was slurried in ethyl acetate (25 ml) followed by water (50 ml). The solid was isolated by filtration to give (16) as a yellow solid (2.1 g, 60%).

ESI [M+H]$^+$481

Further illustrative compound of the invention are:

4,5-Bis(1,1-difluorocyclohexyl-4-carbonyloxy)-9,10-dioxo-9,10-dihydroanthracene-2-carboxylic acid;

4,5-Bis(azetidine-3-carbonyloxy)-9,10-dioxo-9,10-dihydroanthracene-2-carboxylic acid; and 4,5-Bis(morpholine-4-acetyloxy)-9,10-dioxo-9,10-dihydroanthracene-2-carboxylic acid.

The compound of Example 1 has been shown to have efficacy in the LPS mouse and rat EAE models.

LPS Mouse Assay 7 week old Balb-c mice (n=8) fed and watered ad libitum were dosed at time zero with the compound of Example 1 at 3, 30 and 300 mg/kg in a 1% methylcellulose vehicle by oral gavage (10 ml/kg). 30 minutes after drug treatment mice were intraperitoneally administered with 1 mg/kg LPS (5 ml/kg in normal saline). 2 hours post-LPS challenge blood samples were collected by cardiac puncture under isoflurane anaesthesia. Blood samples were allowed to clot at room temperature for 10 minutes and then put on ice until spun at 6000 g for 3 minutes at 4° C. and then stored at −20° C. until analysis by ELISA for TNFα and IL-1β levels. TNFα and IL-1β levels were reported as pg/ml of serum (mean±SEM) significance was evaluated by a Dunnett's test followed by a Kruskal-Wallis one way analysis followed by a Dunn's test.

The compound of Example 1 showed significant efficacy on reducing TNFα levels post-LPS insult with all three doses in a dose-dependant manner. Treatment with the compound of Example 1 reduced IL-1β levels at the top two doses. Diacerein was used as an internal positive control in this assay.

Experimental Autoimmune Encephalitis (EAE)

Male Lewis rats (250-290 g) (n=10) were injected into both rear foot-pad with 0.1 ml of an emulsion containing equal parts of guinea-pig spinal cord, phosphate buffered saline and incomplete Freund's adjuvant with 8 mg/ml Mycobacterium tuberculosis H37Ra. The compound of Example 1 (150 mg/kg) was dosed orally in a 10% acacia gum vehicle (1 ml/kg) twice a day from the day of inoculation.

Body weights and neurological scores were observed daily from day 7 post-inoculation. The total daily score was calculated for each group and plotted over time. Non-parametric statistical analyses (Kruskal-Wallis) one-way analysis, followed by a Dunn's test, were employed. The compound of Example 1 showed significant efficacy in the treatment of clinical signs induced in the EAE model.

The invention claimed is:

1. A compound of general formula (I):

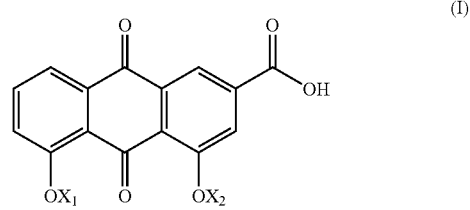

wherein $X_1$ is H or $COR_1$ and $X_2$ is H or $COR_2$ but $X_1$ and $X_2$ are not both H;

$R_1$ and $R_2$ are the same or different and are each $C_{1-4}$ alkyl substituted with $R_3$, or a four to seven-membered ring which is substituted with $R_8$ and can contain one or more heteroatoms selected from O, $S(O)_n$ and $NR_9$;

$R_3$ is $CF_3$, $OR_4$, $NR_5R_6$ or $S(O)_nR_7$;

$R_4$, $R_5$, and $R_6$ are the same or different and are each H or $C_{1-4}$ alkyl optionally substituted with $R_3$, or $NR_5R_6$ is a $C_{4-6}$ heterocycloalkyl ring containing one or more heteroatoms selected from O, $NR_8$ and $S(O)_n$;

each n is 0-2;

$R_7$ is $C_{1-4}$ alkyl;

$R_8$ is as defined for $R_3$ or $C_{1-4}$ alkyl substituted with $R_3$ or halogen; and $R_9$ is H or $C_{1-4}$ alkyl;

or a salt thereof.

2. The compound of claim 1, wherein $X_1$ is $COR_1$ and $X_2$ is $COR_2$.

3. The compound of claim 1, wherein $X_1$ is H and $X_2$ is $COR_2$.

4. The compound of claim 1, wherein $X_1$ is $COR_1$ and $X_2$ is H.

5. A compound which is 4,5-Bis(tetrahydropyran-4-carbonyloxy)-9,10-dioxo-dihydroanthracene-2-carboxylic acid.

6. A compound which is selected from the group consisting of is;
- 4,5-bis(2-benzyloxyacetyloxy)-9,10-dioxo-9,10-dihydroanthracene-2-carboxylic acid;
- 4,5-bis(4-methoxybutyryloxy)-9,10-dioxo-9,10-dihydroanthracene-2-carboxylic acid; or
- 4,5-bis(tetrahydrofuran-3-carbonyloxy)-9,10-dioxo-9,10-dihydroanthracene-2-carboxylic acid.

7. A pharmaceutical composition, comprising a pharmaceutically acceptable diluent or carrier and a compound of general formula (I):

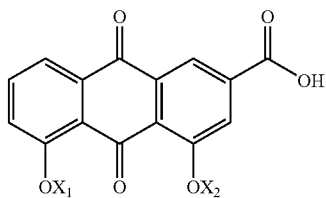

(I)

wherein $X_1$ is H or $COR_1$ and $X_2$ is H or $COR_2$ but $X_1$ and $X_2$ are not both H;

$R_1$ and $R_2$ are the same or different and are each $C_{1-4}$ alkyl substituted with $R_3$, or a four to seven-membered ring which can be optionally substituted with $R_8$ and can contain one or more additional heteroatoms selected from O, $S(O)_n$ and $NR_9$;

$R_3$ is $CF_3$, $OR_4$, $NR_5R_6$ or $S(O)_nR_7$;

$R_4$, $R_5$, and $R_6$ are the same or different and are each H or $C_{1-4}$ alkyl optionally substituted with $R_3$, or $NR_5R_6$ is a $C_{4-6}$ heterocycloalkyl ring containing one or more heteroatoms selected from O, $NR_8$ and $S(O)_n$;

each n is 0-2;

$R_7$ is $C_{1-4}$ alkyl;

$R_8$ is as defined for $R_3$ or $C_{1-4}$ alkyl optionally substituted with $R_3$ or halogen; and $R_9$ is H or $C_{1-4}$ alkyl;

or a salt thereof.

* * * * *